United States Patent
MacNeish, III et al.

(10) Patent No.: US 8,712,494 B1
(45) Date of Patent: Apr. 29, 2014

(54) REFLECTIVE NON-INVASIVE SENSOR

(75) Inventors: William Jack MacNeish, III, Costa Mesa, CA (US); Eugene E. Mason, La Habra Heights, CA (US); John Schmidt, Huntington Beach, CA (US); Chad Cory Eichele, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 394 days.

(21) Appl. No.: 13/099,263

(22) Filed: May 2, 2011

Related U.S. Application Data

(60) Provisional application No. 61/330,666, filed on May 3, 2010, provisional application No. 61/331,087, filed on May 4, 2010.

(51) Int. Cl.
*A61B 5/1455* (2006.01)

(52) U.S. Cl.
USPC .......................... 600/344; 600/322; 600/310

(58) Field of Classification Search
USPC ................................. 600/309–344
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |

(Continued)

*Primary Examiner* — Eric Winakur
*Assistant Examiner* — Marjan Fardanesh
(74) *Attorney, Agent, or Firm* — Knobbe, Martens, Olson & Bear LLP

(57) ABSTRACT

Aspects of the present disclosure include a sensor emitter including a reflective cavity for re-directing light to a tissue site. By reflecting light towards the tissue site, the amount of light reaching the tissue site is increased. The increased light can improve parameter measurements taken by a non-invasive physiological sensor by producing a stronger and/or cleaner signal. In an embodiment, the reflective cavity is formed on one or more lead frames of the sensor emitter, wherein the lead frames are capable of transmitting electrical signals to emitting elements coupled to the lead frames. Aspects of the present disclosure also include a sensor component configured to protect connection points of wires to conductive leads on the sensor components by inhibiting flex or bending at the connection points. Connection points can protrude along edges of the sensor component. Aspects of the present disclosure also include techniques and processes for producing low-profile sensors.

19 Claims, 13 Drawing Sheets

(56) References Cited

U.S. PATENT DOCUMENTS

| | | |
|---|---|---|
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |

(56) References Cited

U.S. PATENT DOCUMENTS

| | | |
|---|---|---|
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 2002/0107436 A1* | 8/2002 | Barton et al. ............... 600/382 |
| 2009/0177053 A1* | 7/2009 | Merchant et al. ............. 600/323 |

\* cited by examiner

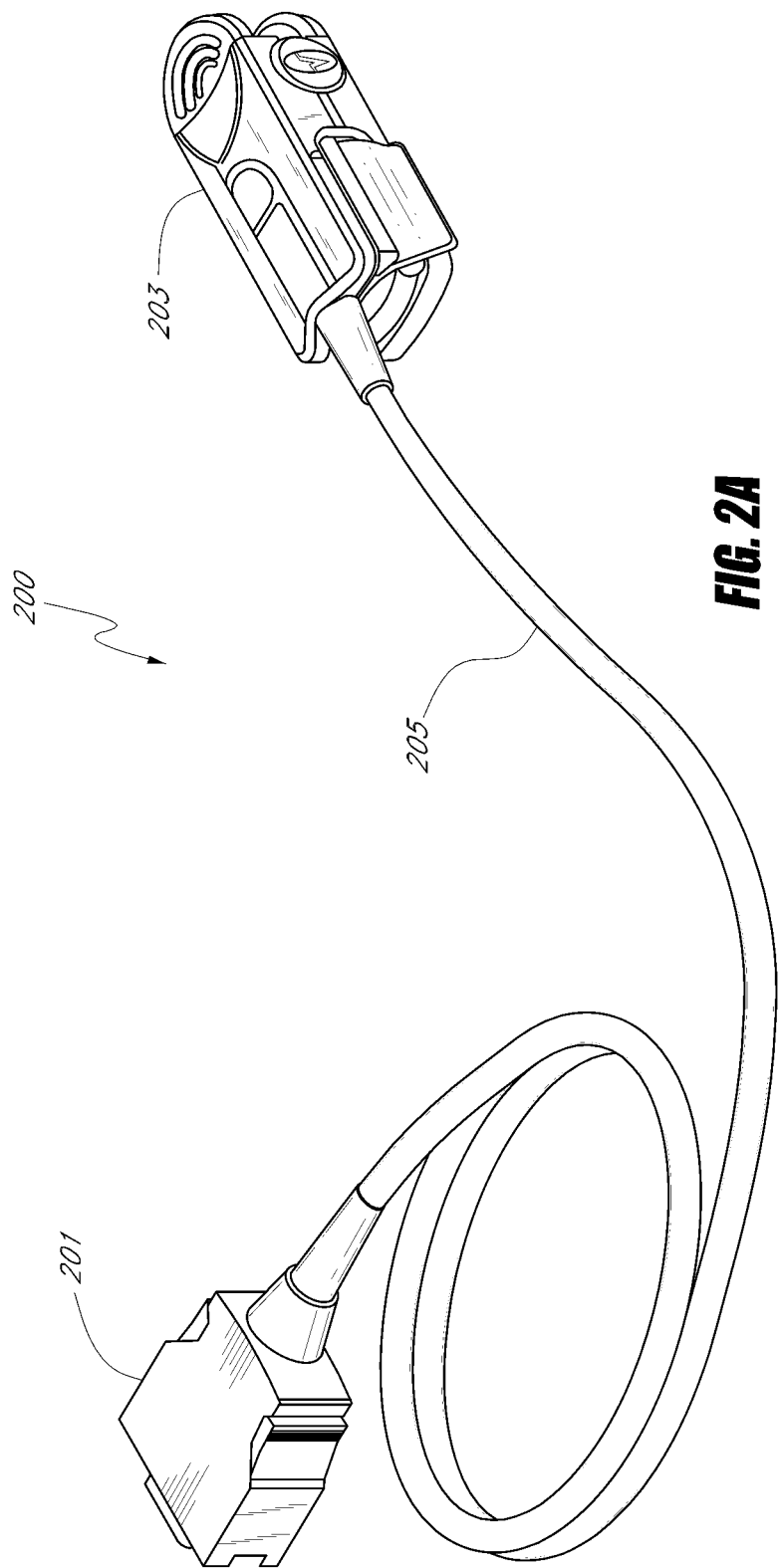

REFLECTIVE NON-INVASIVE SENSOR

CROSS-REFERENCE TO RELATED APPLICATIONS

This application claims the benefit of priority under 35 U.S.C. §119(e) of U.S. Provisional Application No. 61/330,666, filed May 3, 2010, titled LOW PROFILE NON-INVASIVE SENSOR and U.S. Provisional Application No. 61/331,087, filed May 4, 2010, titled ACOUSTIC RESPIRATION DISPLAY, the entire contents of which are hereby incorporated by reference herein.

FIELD OF THE DISCLOSURE

The disclosure relates to the field of physiological sensors, and more specifically to emitters and detectors for physiological sensors.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to SpO2, such as HbCO, HbMet and/or Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp.

SUMMARY OF THE DISCLOSURE

Aspects of the present disclosure include a sensor emitter including a reflective cavity for re-directing light to a tissue site. By reflecting light towards the tissue site, the amount of light reaching the tissue site is thereby increased. The increased light can improve parameter measurements taken by a non-invasive physiological sensor by producing a stronger and/or cleaner signal. In an embodiment, the reflective cavity is formed on one or more lead frames of the sensor emitter, wherein the lead frames are capable of transmitting electrical signals to emitting elements coupled to the lead frames.

Aspects of the present disclosure also include a sensor component configured to protect connection points of wires to conductive leads on the sensor components by inhibiting flex or bending at the connection points. In an embodiment, connection points protrude along edges of the sensor component.

Aspects of the present disclosure also include techniques and processes for producing low-profile sensors.

BRIEF DESCRIPTION OF THE DRAWINGS

Throughout the drawings, reference numbers may be re-used to indicate correspondence between referenced elements. The drawings are provided to illustrate embodiments of the disclosure described herein and not to limit the scope thereof.

FIGS. 2A-C illustrate several embodiments of sensor assemblies;

DETAILED DESCRIPTION

Figure 1:
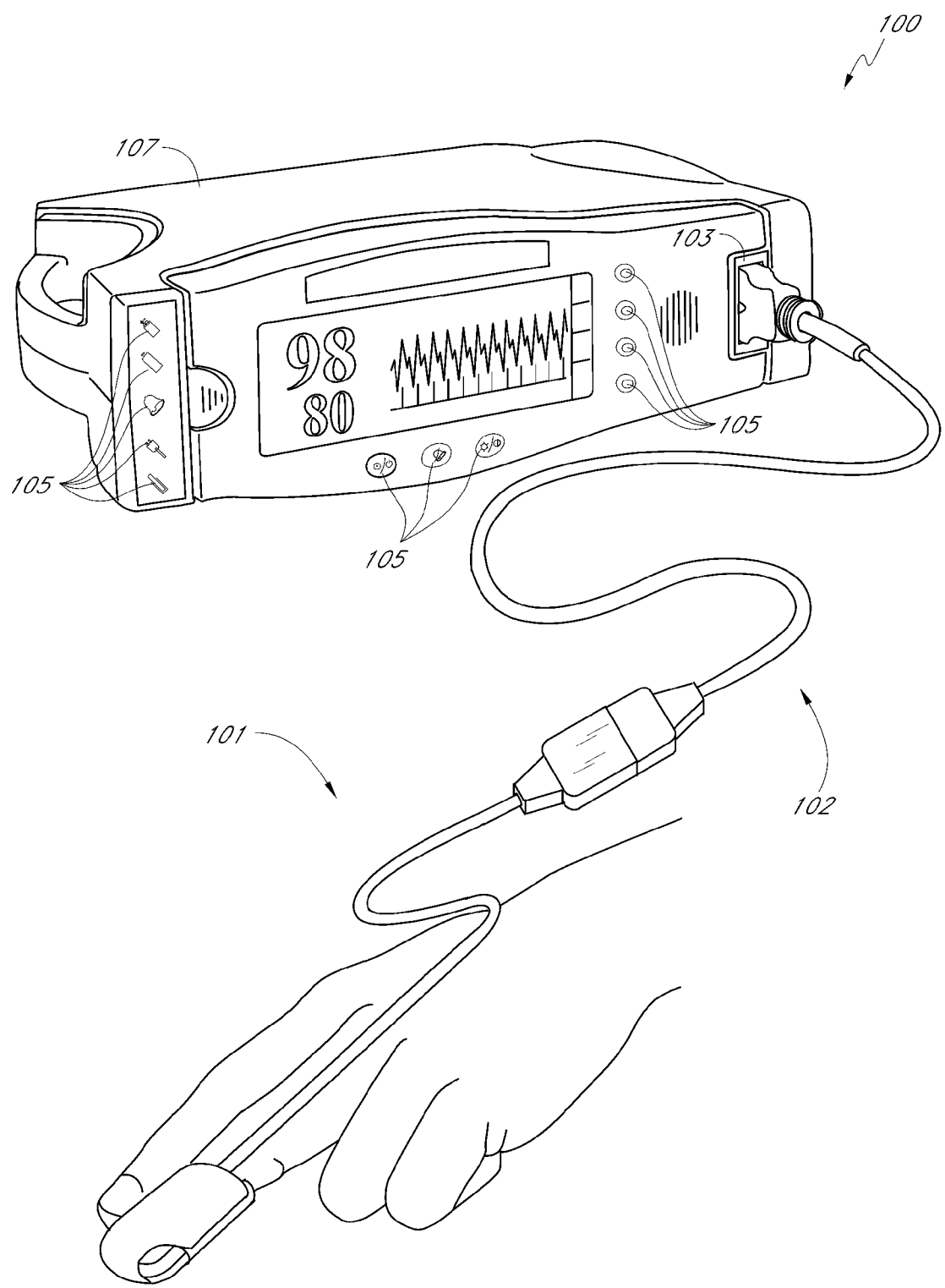
FIG. 1 illustrates an embodiment of a physiological measurement system.

FIG. 1 illustrates an embodiment of a physiological measurement system 100 having a monitor 107 and a sensor assembly 101. The physiological measurement system 100 allows the monitoring of a person, including a patient. In particular, the multiple wavelength sensor assembly 101 allows the measurement of blood constituents and related parameters, including, for example, oxygen saturation, HbCO, HBMet and pulse rate, among others.

In an embodiment, the sensor assembly 101 is configured to plug into a monitor sensor port 103. Monitor keys 105 provide control over operating modes and alarms, to name a few. A display 107 provides readouts of measured parameters, such as oxygen saturation, pulse rate, HbCO and HbMet to name a few.

FIG. 2A illustrates a multiple wavelength sensor assembly 200 having a sensor 203 adapted to attach to a tissue site, a sensor cable 205 and a monitor connector 201. In an embodiment, the sensor 203 is incorporated into a reusable finger clip adapted to removably attach to, and transmit light through, a fingertip. The sensor cable 205 and monitor connector 201 are integral to the sensor 203, as shown. In embodiments, the sensor 203 can be configured separately from the cable 205 and connector 201, although such communication can advantageously be wireless, over public or private networks or computing systems or devices, through intermediate medical or other devices, combinations of the same, or the like.

Figure 2B:
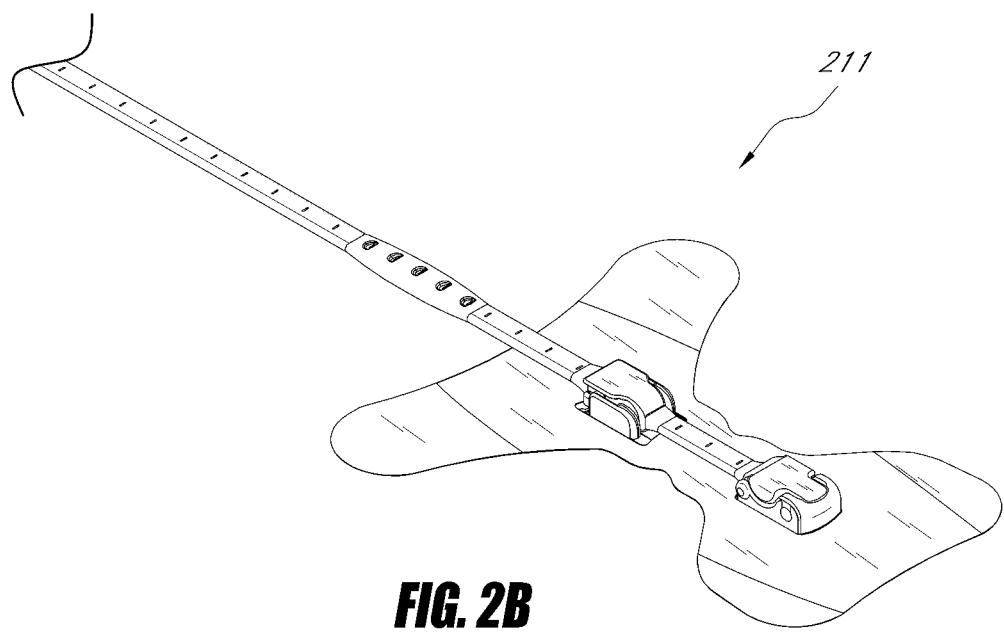
Figure 2C:
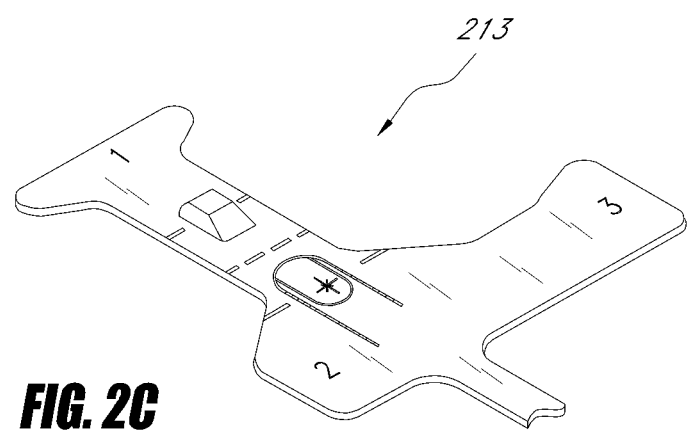

FIGS. 2B-C illustrate alternative sensor embodiments, including a sensor 211 (FIG. 2B) partially disposable and partially reusable (resposable) and utilizing an adhesive attachment mechanism. Also shown is a disposable sensor 213 utilizing an adhesive attachment mechanism. The sensor can include one or more flexible tape layers. In other embodiments, a sensor can be configured to attach to various tissue sites other than a finger, such as a foot or an ear. Also, a sensor can be configured as a reflectance or transflectance device that attaches to a forehead or other tissue surface. The artisan will recognize from the disclosure herein that the sensor can include mechanical structures, adhesive or other tape structures, Velcro® wraps or combination structures specialized for the type of patient, type of monitoring, type of monitor, or the like.

Figure 3:
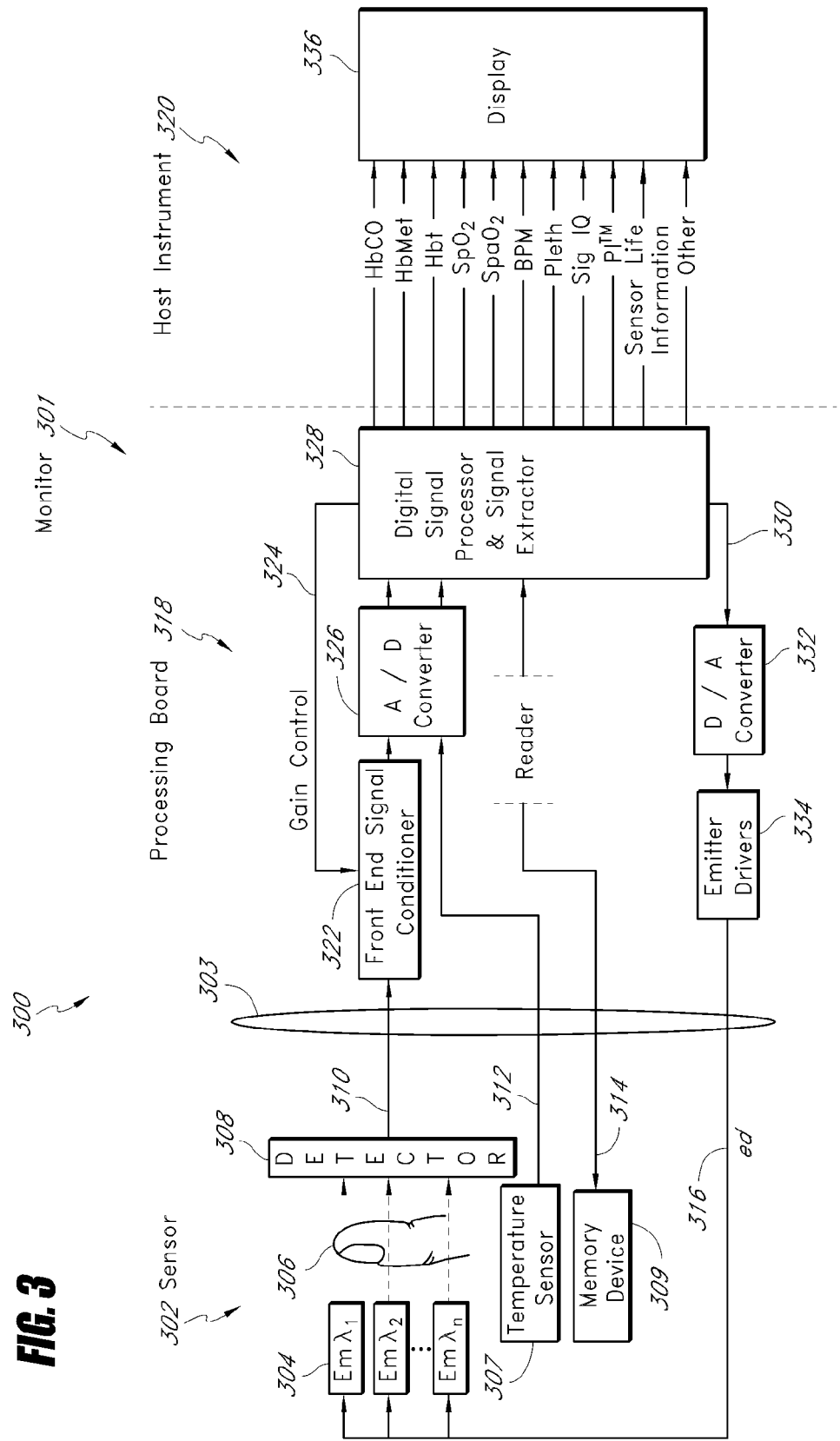
FIG. 3 illustrates a block diagram of an embodiment of an oximetry system.

FIG. 3 illustrates a block diagram of an exemplary embodiment of a monitoring system 300. As shown in FIG. 3, the monitoring system 300 includes a monitor 301, a noninvasive sensor 302, communicating through a cable 303. In an embodiment, the sensor 302 includes a plurality of emitters 304 irradiating the body tissue 306 with light, and one or more detectors 308 capable of detecting the light after attenuation by tissue 306. As shown in FIG. 3, the sensor 302 also includes a temperature sensor 307, such as, for example, a thermistor or the like. The sensor 302 also includes a memory device 309 such as, for example, an electrically erasable programmable read only memory (EEPROM), erasable programmable read only memory (EPROM), flash memory, nonvolatile memory or the like. The sensor 302 also includes a plurality of conductors communicating signals to and from its components, including detector composite signal conductors 310, temperature sensor conductors 312, memory device conductors 314, and emitter drive signal conductors 316.

According to an embodiment, the sensor conductors 310, 312, 314, 316 communicate their signals to the monitor 301 through the cable 303. Although disclosed with reference to the cable 303, a skilled artisan will recognize from the disclosure herein that the communication to and from the sensor 306 can advantageously include a wide variety of cables, cable designs, public or private communication networks or computing systems, wired or wireless communications (such as Bluetooth® or WiFi, including IEEE 801.11a, b, g, or n), mobile communications, combinations of the same, or the like. In addition, communication can occur over a single wire or channel or multiple wires or channels.

In an embodiment, the temperature sensor 307 monitors the temperature of the sensor 302 and its components, such as, for, example, the emitters 304. For example, in an embodiment, the temperature sensor 307 includes or communicates with a thermal bulk mass having sufficient thermal conduction to generally approximate a real-time temperature of a substrate of the light emission devices 304. The foregoing approximation can advantageously account for the changes in surface temperature of components of the sensor 302, which can change as much or more than ten degrees Celsius (10° C.) when the sensor 302 is applied to the body tissue 306. In an embodiment, the monitor 101 can advantageously use the temperature sensor 307 output to, among other things, ensure patient safety, especially in applications with sensitive tissue. In an embodiment, the monitor 301 can advantageously use the temperature sensor 307 output and monitored operating current or voltages to correct for operating conditions of the sensor 302 as described in U.S. patent application Ser. No. 11/366,209, filed Mar. 1, 2006, entitled "Multiple Wavelength Sensor Substrate," and herein incorporated by reference.

The memory 309 can include any one or more of a wide variety of memory devices known to an artisan from the disclosure herein, including an EPROM, an EEPROM, a flash memory, a combination of the same or the like. The memory 309 can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the memory 309 can include the ROM, the RAM, single wire memories, combinations, or the like.

The memory device 309 can advantageously store some or all of a wide variety data and information, including, for example, information on the type or operation of the sensor 302, type of patient or body tissue 306, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the memory device 309 can also include emitter wavelength correction data.

In an advantageous embodiment, the monitor reads the memory device on the sensor to determine one, some or all of a wide variety of data and information, including, for example, information on the type or operation of the sensor, a type of patient, type or identification of sensor buyer, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters it is intended to measure (e.g., HbCO, HbMet, etc.) calibration data, software such as scripts, executable code, or the like, sensor electronic elements, whether it is a disposable, reusable, or multi-site partially reusable, partially disposable sensor, whether it is an adhesive or non-adhesive sensor, whether it is reflectance or transmittance sensor, whether it is a finger, hand, foot, forehead, or ear sensor, whether it is a stereo sensor or a two-headed sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

FIG. 3 also shows the monitor 301 comprising one or more processing boards 318 communicating with one or more host instruments 320. According to an embodiment, the board 318 includes processing circuitry arranged on one or more printed circuit boards capable of installation into the handheld or other monitor 301, or capable of being distributed as an OEM component for a wide variety of host instruments 320 monitoring a wide variety of patient information, or on a separate unit wirelessly communicating to it. As shown in FIG. 3, the board 318 includes a front end signal conditioner 322 including an input receiving the analog detector composite signal from the detector 308, and an input from a gain control signal 324. The signal conditioner 322 includes one or more outputs communicating with an analog-to-digital converter 326 ("A/D converter 326").

The A/D converter 326 includes inputs communicating with the output of the front end signal conditioner 322 and the output of the temperature sensor 307. The converter 326 also includes outputs communicating with a digital signal processor and signal extractor 328. The processor 328 generally communicates with the A/D converter 326 and outputs the gain control signal 324 and an emitter driver current control signal 330. The processor 328 also communicates with the memory device 309. As shown in phantom, the processor 328 can use a memory reader, memory writer, or the like to communicate with the memory device 309. Moreover, FIG. 3 also shows that the processor 328 communicates with the host instrument 320 to for example, display the measured and calculated parameters or other data.

FIG. 3 also shows the board 318 including a digital-to-analog converter 332 ("D/A converter 332") receiving the current control signal 330 from the processor 328 and supplying control information to emitter driving circuitry 334, which in turns drives the plurality of emitters 304 on the sensor 302 over conductors 316. In an embodiment, the emitter driving circuitry 334 drives sixteen (16) emitters capable of emitting light at sixteen (16) predefined wavelengths, although the circuitry 334 can drive any number of emitters. For example, the circuitry 334 can drive two (2) or more emitters capable of emitting light at two (2) or more wavelengths, or it can drive a matrix of eight (8) or more emitters capable of emitting light at eight (8) or more wavelengths. In addition, one or more emitters could emit light at the same or substantially the same wavelength to provide redundancy. In one embodiment, the emitters emit light at red and infrared wavelengths, for example 660 nm (R) and 905 nm (IR).

In an embodiment, the host instrument 320 communicates with the processor 328 to receive signals indicative of the physiological parameter information calculated by the processor 328. The host instrument 320 preferably includes one or more display devices 336 capable of providing indicia representative of the calculated physiological parameters of the tissue 306 at the measurement site. In an embodiment, the host instrument 320 can advantageously includes virtually any housing, including a handheld or otherwise portable monitor capable of displaying one or more of the foregoing measured or calculated parameters. In still additional embodiments, the host instrument 320 is capable of displaying trending data for one or more of the measured or determined parameters. Moreover, an artisan will recognize from the disclosure herein many display options for the data available from the processor 328.

In an embodiment, the host instrument 320 includes audio or visual alarms that alert caregivers that one or more physiological parameters are falling below or above predetermined safe thresholds, which are trending in a predetermined direction (e.g., good or bad), and can include indications of the confidence a caregiver should have in the displayed data. In further embodiment, the host instrument 320 can advantageously include circuitry capable of determining the expiration or overuse of components of the sensor 302, including, for example, reusable elements, disposable elements, combinations of the same, or the like. Moreover, a detector could advantageously determine a degree of clarity, cloudiness, transparence, or translucence over an optical component, such as the detector 308, to provide an indication of an amount of use of the sensor components and/or an indication of the quality of the photo diode.

An artisan will recognize from the disclosure herein that the emitters 304 and/or the detector 308 can advantageously be located inside of the monitor, or inside a sensor housing. In such embodiments, fiber optics can transmit emitted light to and from the tissue site. An interface of the fiber optic, as opposed to the detector can be positioned proximate the tissue. In an embodiment, the physiological monitor accurately monitors HbCO in clinically useful ranges. This monitoring can be achieved with non-fiber optic sensors. In another embodiment, the physiological monitor utilizes a plurality, or at least four, non-coherent light sources to measure one or more of the foregoing physiological parameters. Similarly, non-fiber optic sensors can be used. In some cases the monitor receives optical signals from a fiber optic detector. Fiber optic detectors are useful when, for example, monitoring patients receiving MRI or cobalt radiation treatments, or the like. Similarly, light emitters can provide light from the monitor to a tissue site with a fiber optic conduit. Fiber optics are particularly useful when monitoring HbCO and HbMet. In another embodiment, the emitter is a laser diode place proximate tissue. In such cases, fiber optics are not used. Such laser diodes can be utilized with or without temperature compensation to affect wavelength.

Figure 4A:
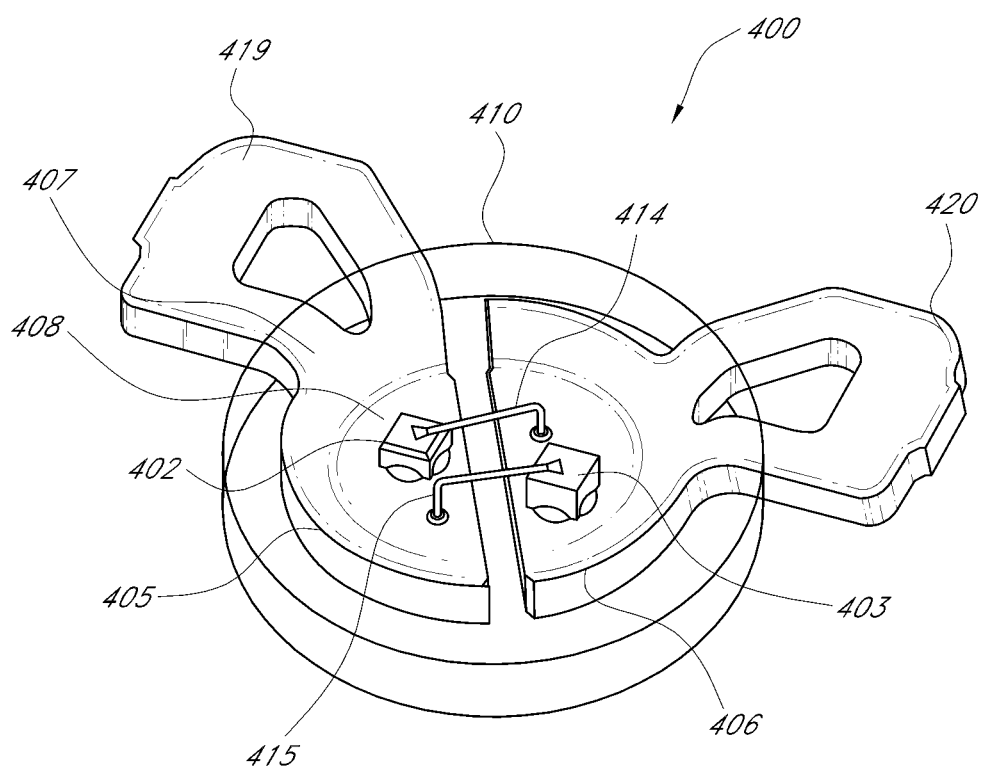
FIG. 4A illustrates a perspective view of the tissue-facing side of an embodiment of a sensor emitter of a sensor.

FIG. 4A illustrates a perspective view of the tissue-facing side of an embodiment of a sensor emitter 400. In an embodiment, the sensor emitter is incorporated into a sensor, such as the sensor embodiments described above. The sensor emitter can include one or more emitters or emitting elements 402, 403, one or more lead frames 405, 406 and an encapsulate 410. In an embodiment, the sensor emitter 400 is a two-lead configuration having two emitters. The emitting elements 402, 403 can be light emitting diodes (LEDs) or other light emitting devices. In one embodiment, the LEDs are configured to transmit light in different wavelengths. In FIG. 4A, the emitting elements 402, 403 are electrically and/or mechanically connected to respective lead frames 405, 406. In some embodiments, the lead frames are at least partially reflective on the tissue-facing side where the emitting elements are connected, for example, due to the selected lead frame material. In an embodiment, the lead frame's reflectiveness is enhanced by polishing or by plating by another material, for example silver, or the like. The encapsulate 410 can act as a mechanical support for the lead frames 405, 406.

The encapsulate 410 can be formed out of epoxy, plastic, ceramic, or other material and can be formed by processes such as, for example, molding, injecting, rolling, pressing, casting, extruding, or other processes as would be understood by those of skill in the art from the present disclosure. In one embodiment, the encapsulate wholly encloses the emitting elements and portions of the lead frame in order to protect those elements from damage and/or wear. The encapsulate can also serve to mechanically couple elements of the sensor. In one embodiment, the encapsulate forms a low-profile shape, such as a disc, oblong, cuboid, rectangular box, or the like, wherein width and depth are generally larger than height, allowing the creation of low-profile sensor components. In one embodiment, the encapsulate can be transparent or translucent.

The lead frames 405, 406 can be incorporated in the encapsulate 410, for example, during manufacture. The lead frame material can include tungsten, copper, silver, silver-filled thermoplastic, nickel, gold, copper, any other conductive material, or other suitable material as would be understood by those of skill in the art from the present disclosure. The encapsulate 410 can electrically isolate at least portions of the lead frames. For example, the encapsulate can prevent a first lead frame 405 from electrically connecting with a second lead frame 406, for example, by fixing the positions of the frames and maintaining a space between the frames.

In some embodiments, one or more lead frames 405, 406 taken as a whole form a cavity. For example, if the first lead frame 405 and the second lead frame 406 were joined together, a cavity having a cavity bottom and cavity sides can be defined by portions 407, 408 of the lead frames. The cavity can be formed in multiple lead frames, with sections of the cavity on each lead frame. The cavity can be shaped similarly to a parabola, a bowl, a frustum, a truncated pyramid or cone, or the like. The cavity sides and/or cavity bottom can be advantageously formed to permit or restrict light to reach the emitting elements. The cavity sides and/or cavity bottom can be flat, rounded, diagonally cut, sloped or formed in other shapes advantageous to either permit or restrict light to reach the emitting elements, to enhance properties of the encapsulate including, but not limited to, structural and manufacturing concerns, to assist in the interface of the emitters with the encapsulate, or to enhance the performance of the sensor emitter 400.

In one embodiment, the cavity side can include an angled portion 407 of a lead frame 405 while a cavity bottom can include a generally flat portion 408 of the lead frame 405, on which an emitting element 402 can be attached. The angled portion can form an arc or one or more sides around the generally flat portion. The angled portion and/or flat portion can be formed on an at least semi-reflective surface of the lead frame in order to reflect light outward from the emitting elements into the tissue site, thereby directing more light generated by the emitting elements towards the tissue site. Thus, usable light can be increased and/or light diffusion can be reduced.

In an embodiment, the encapsulate 410 acts as an electrical insulator allowing multiple lead frames 405, 406 to be electrically insulated from each other. In one embodiment, a first wire bond 414 electrically connects a first emitting element 402 on a first lead frame 405 to a second lead frame 406. A second wire bond 415 can connect a second emitting element 403 on the second lead frame 406 to the first lead frame 405. In one embodiment, the emitting elements comprise LEDs or diodes that allow current to flow in only one direction. Thus, in one embodiment, current from the first lead frame 405 to the second lead frame 406 flows on one wire bond, while current from the second lead frame to the first lead frame flows on another other wire bond. In the described configuration, the wire bonds and diodes form an inverse parallel circuit. As the lead frames in the described configuration are electrically insulated from each other by the encapsulate and electrically connected only through the uni-directional wire bonds and emitting elements, the first or the second emitting element can be selectively activated based on the direction of the current flow.

In some embodiments, the lead frame 405, 406 can protrude outward to the sides of the encapsulate 410. The protruding portions 419, 420 can allow electrical connections to be formed with wires, conductive substrates, or other conductive material in order to transmit electrical signals to and/or from a monitor and/or provide power to the sensor component. Electrical coupling can be by, for example, soldering, wire bonding, die bonding, or other suitable forms of electrical connection. In an embodiment, the emitting elements 402, 403 can be placed near the connection points in order to allow the connecting wires and/or coupling material to act as a heatsink for the emitting elements.

Figure 4B:
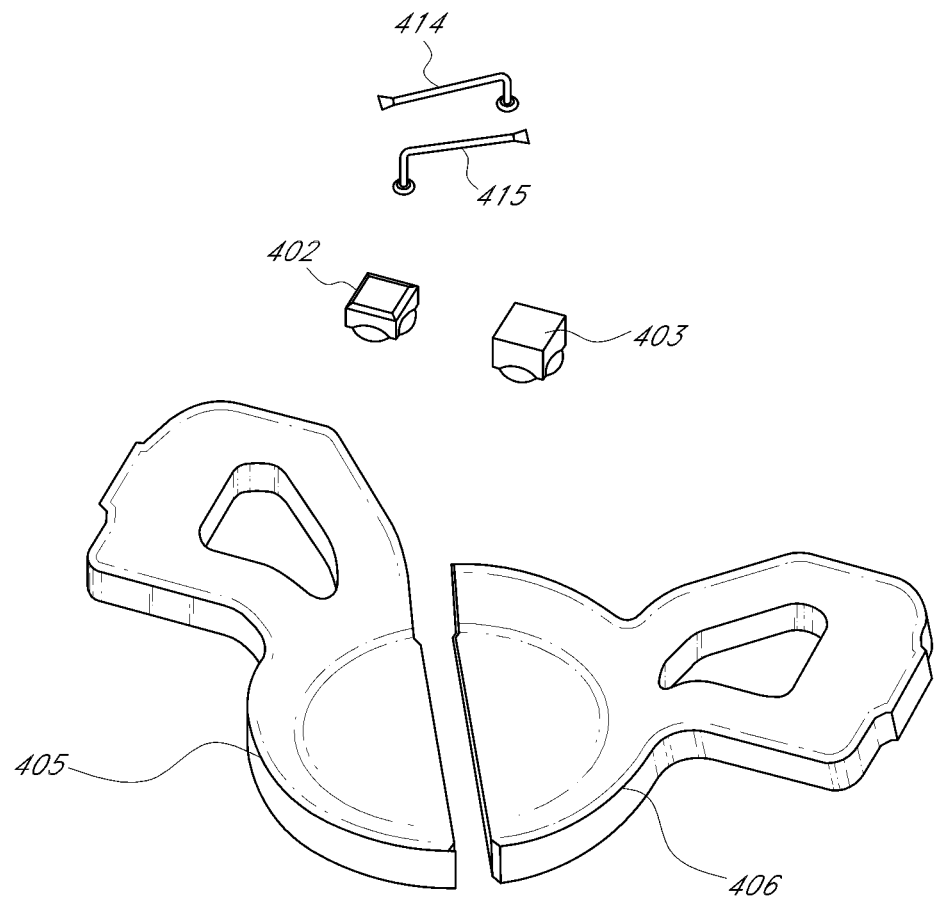
FIG. 4B illustrates an exploded view of the sensor emitter embodiment of FIG. 4A.

FIG. 4B illustrates an exploded view of the sensor emitter embodiment of FIG. 4A. The sensor emitter can include one or more lead frames 405, 406, one or more emitting elements 402, 403, and one or more wire bonds 414, 415.

Figure 5A:
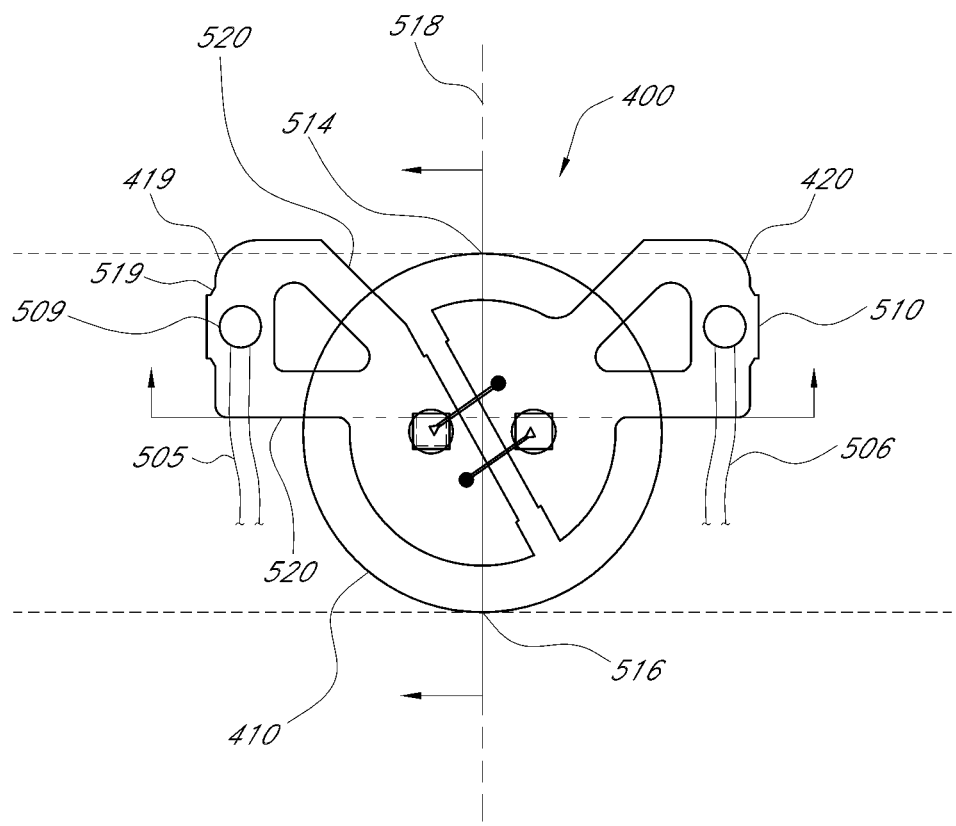
FIG. 5A illustrates a top view of the sensor emitter embodiment of FIG. 4.

FIG. 5A illustrates a top view of the sensor emitter embodiment of FIG. 4. The sensor emitter 400 can be electrically coupled in any way to wires 505, 506 or other conductive material via the connection points 509, 510 on the lead frame protrusions 419, 420. For example, the sensor emitter can be mounted to wires or to a sensor surface with embedded leads. The wires 505, 506 are configured to connect with the sensor emitter 400 such that the connection points 509, 510 are between a distal 514 and a proximal 516 end of the sensor emitter relative to a sensor cable and/or sensor cable connector. In one embodiment, the wires 505, 506 are configured to lie generally parallel to an axis 518 from the distal 514 to the proximal 516 end of the sensor emitter. The encapsulate can function as a spacer and/or insulator between the wires and/or leads, preventing electrical bridging between the wires and/or leads.

In one embodiment, the bottom of the sensor emitter 400 is attached to an at least semi-flexible or flexible substrate, such as a tape layer, of a sensor. The flexible substrate can include conductive leads or wires. For example, the flexible substrate can comprise a flexible circuit. In one embodiment, the encapsulate 410 material is generally rigid or semi-rigid, inhibiting flexing of a portion of the wires 505, 506 and/or flexible substrate around the sensor emitter. In some embodiments, the lead frame protrusions 419, 420 can extend for some length generally parallel to the axis 518 and/or wires 505, 506 in order to further inhibit flexing around the sensor emitter. For example, the lead frame protrusion 419 can have a generally straight portion 519 extending in a direction along the axis 518 with one or more supports 520 connecting the generally straight portion to the lead frame 405. By positioning the connection points on the sides of the sensor emitter, the connection points can be advantageously protected from flexing of the wires or substrate by the sensor emitter body. Thus, by inhibiting flexing at the connection points, the durability of the sensor is enhanced, for example, by inhibiting disconnection of wires 505, 506 with the sensor emitter 400, limiting stress on the connection points, and/or reducing wear and tear at the connection points.

Figure 5B:
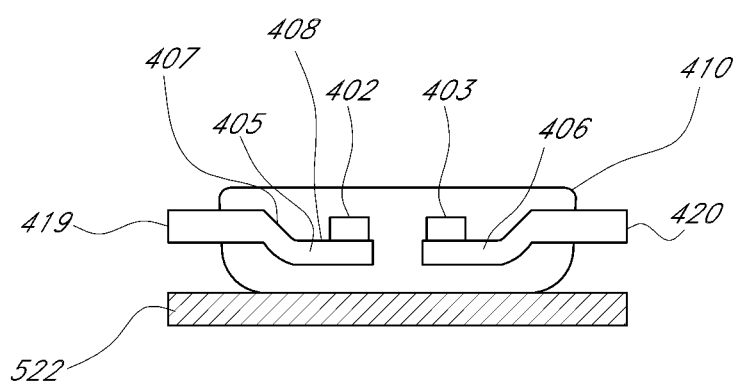
FIG. 5B illustrates a cross sectional view of the sensor emitter embodiment of FIG. 5A.

FIG. 5B illustrates a cross sectional view of the sensor emitter embodiment of FIG. 5A. In the illustrated embodiment, the first lead frame 405 is electrically isolated from the second lead frame 406 by the encapsulate 410. Protruding portions 419, 420 of the lead frames can extend past the encapsulate, providing a connection point for wires or cables. A first emitting element 402 can be positioned on the first frame 405 and a second emitting element 403 can be positioned on the second frame 406. The first frame and second frame can form a cavity configured to reflect light towards the tissue site. The cavity can be formed by an angled portion 407 and a flat portion 408 of the lead frames 405, 406. In an embodiment, the angled portion of the lead frames can extend to or near the top surface of the encapsulate in order reduce light diffusion or escape, which can cause signal artifacts in parameter measurements.

In some embodiments, the sensor emitter can be coupled to a sensor portion 522, such as a sensor body, a tape layer, or the like, on the sensor emitter bottom or side opposite the tissue site. In some embodiments, another sensor portion, such as a cover, tape layer, or the like, can cover the top or tissue facing side of the sensor emitter. In an embodiment, wires are configured to run between the protruding portions 419, 420 and the sensor portion 522, placing the wires away from the tissue site in order to reduce patient discomfort. The placement of the wires between the two portions can also provide additional mechanical support for the wires, inhibiting disconnection of the wires from the sensor emitter.

Figure 5C:
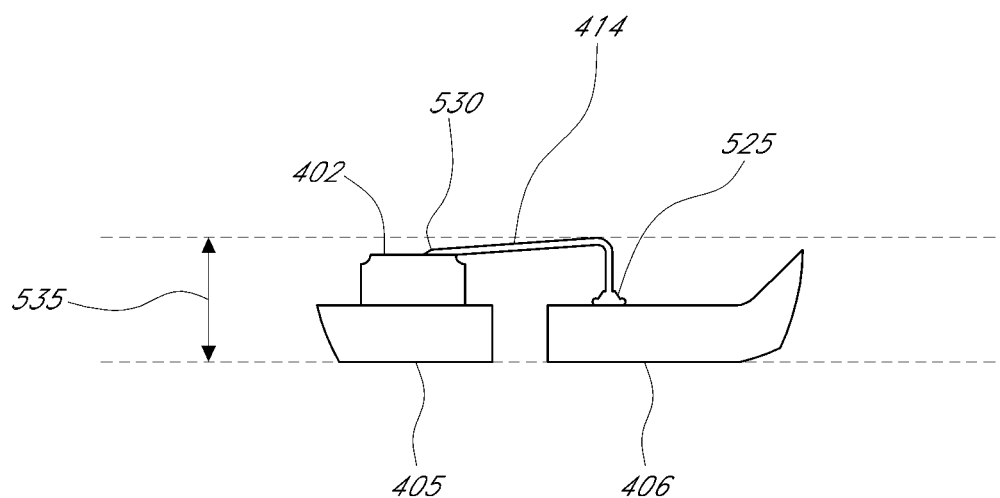
FIG. 5C illustrates a side view of an embodiment of a reverse wire bond connection.

FIG. 5C illustrates a side view of an embodiment of a reverse wire bond connection. A reverse wire bond 414 can be used to reduce the height of the sensor. In a reverse wire bond, a ball bond 525 is formed on the lead frame 406 while a wedge or tail bond 530 is formed on the emitting element 402 on the other lead frame 405. As the lead frame 406 is lower than the top of the emitting element, by placing the ball bond on the lead frame, the height 535 of the reverse wire bond is lower than a regular wire bond where the ball bond is on the emitting element. Thus, the reverse wire bond allows the formation of lower-profile sensors compared to a regular wire bond. In one embodiment, the height 535 of the lead frame 406 and wire bond 525 defines a minimum possible profile of the sensor.

Figure 6:
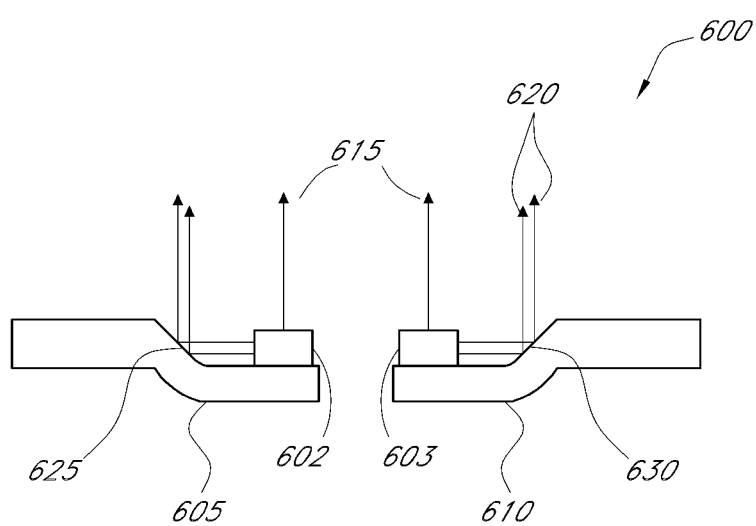
FIG. 6 illustrates a depiction of light waves emanating from one embodiment of the sensor emitter.

FIG. 6 illustrates a depiction of light waves emanating from one embodiment of the sensor emitter. In some embodiments, the emitting elements 602, 603 emit light in multiple directions. Some of the light 615 ("direct light") can be directly transmitted from the emitting elements to the tissue site. Some of the light 620 ("indirect light") is originally transmitted to a different direction from the tissue site but can be redirected towards the tissue site by elements of the sensor emitter 625, 630, such as portions of lead frames or other reflective surfaces. For example, portions of the lead frames can be angled towards the tissue site in order to redirect light.

By redirecting light, the amount of usable light, including direct and indirect light, can be increased. The increased usable light can improve parameter measurements by producing a stronger and/or cleaner signal. For example, the detector can receive more light attenuated by the tissue and/or receive less light not attenuated by the tissue.

Advantageously, by using a reflective cavity, a weaker emitting element can be used while providing the same amount of usable light as a stronger emitting element not using a reflective cavity. In some cases, the weaker emitting element can be cheaper, require less power, have a longer operating life, or provide some other benefit in comparison to the stronger emitting element. For example, an emitting element with a lower power draw can increase the operating time of the sensor when connected to a stored power source, such as a battery.

In one embodiment, the lead frame can be comprised of material configured to meet particular performance specifications ("specced material"), such a reflective quality. If the lead frame material is specced, the variability of the light from the sensor emitter can be reduced in comparison to unspecced material. Generally, large portions of a sensor are comprised of low-cost, unspecced material, such as tape layers, adhesive layers, plastic materials, or the like. Thus, by reflecting much or most of the light from the sensor emitter with a specced reflective surface, the variability can be reduced. For example, if the sensor emitter did not use a specced reflective surface but simply allowed light emanating from the emitter to reflect off of unspecced portions of the sensor, the variability of the light reaching the tissue site can increase. More consistent light can generate a "cleaner" parameter measurement at the tissue site by reducing artifacts or otherwise improving the signal generated by the sensor.

Figure 7:
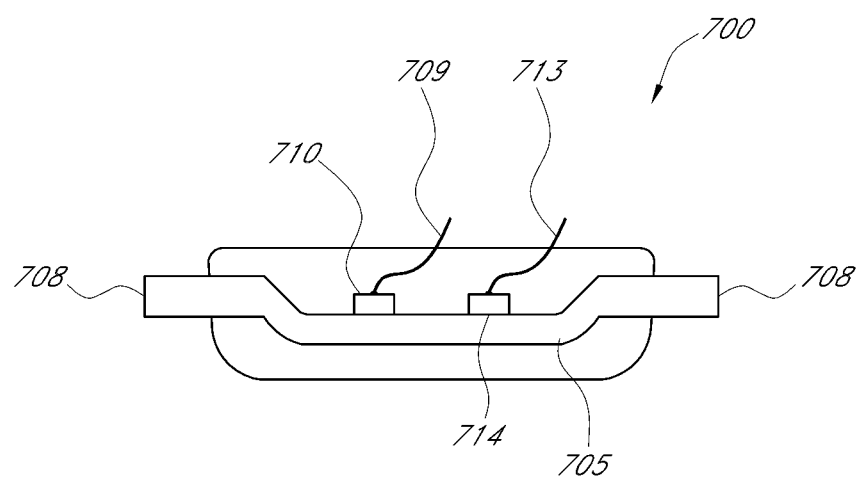
FIG. 7 illustrates a side view of an embodiment of the sensor emitter having a single lead frame.

FIG. 7 illustrates a cross-sectional view of an embodiment of the sensor emitter 700 including a single lead frame 705. A first conductive lead 709 connects to a first emitting element 710 and a second conductive lead 713 connects to a third emitting element 714. A third conductive lead 708 can be formed as part of the lead frame 705. Current on the first lead can activate the first emitting element and current on the second lead can activate the second emitting element. In one embodiment, the first and second leads can be anodes while the third lead is a cathode common to the emitting elements.

Figure 8:
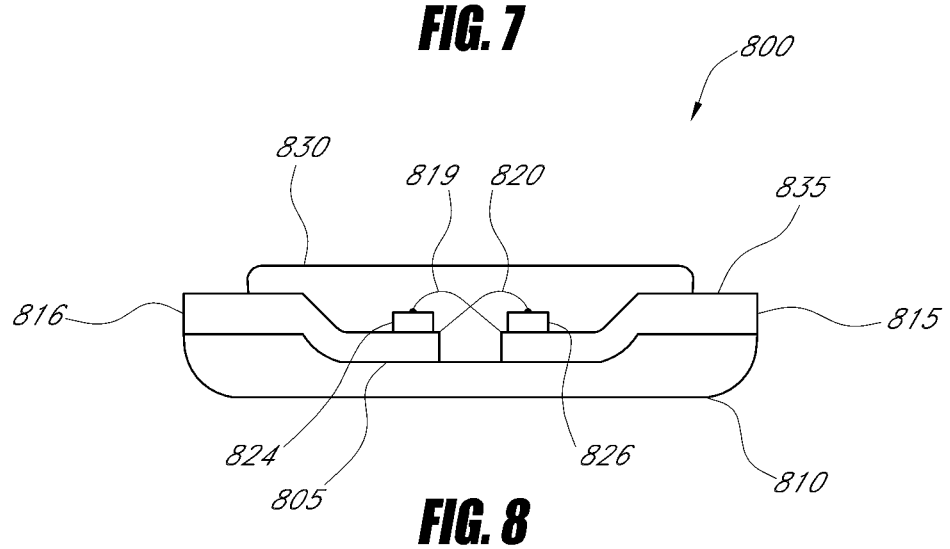
FIG. 8 illustrates a side view of an embodiment of the sensor emitter including a metallization layer.

FIG. 8 illustrates a cross-sectional view of an embodiment of the sensor emitter including a metallization layer. The sensor emitter 800 comprises a cavity 805 formed in the encapsulate 810. A metallization layer 815, 816 is applied onto the cavity. In one embodiment, the metallization layer is formed into electrically distinct sections 815, 816. The metallization layer sections can be electrically connected by wire bond 819, 820 and diodes 824, 826, such as LEDs, as described above. In one embodiment, additional encapsulate material 830 is applied onto the metallization layer and emitting elements in order to form a protective layer over the emitter elements. In one embodiment, portions of the metallization layer 816 can be exposed to allow connection to wires or other conductive material.

Figure 9:
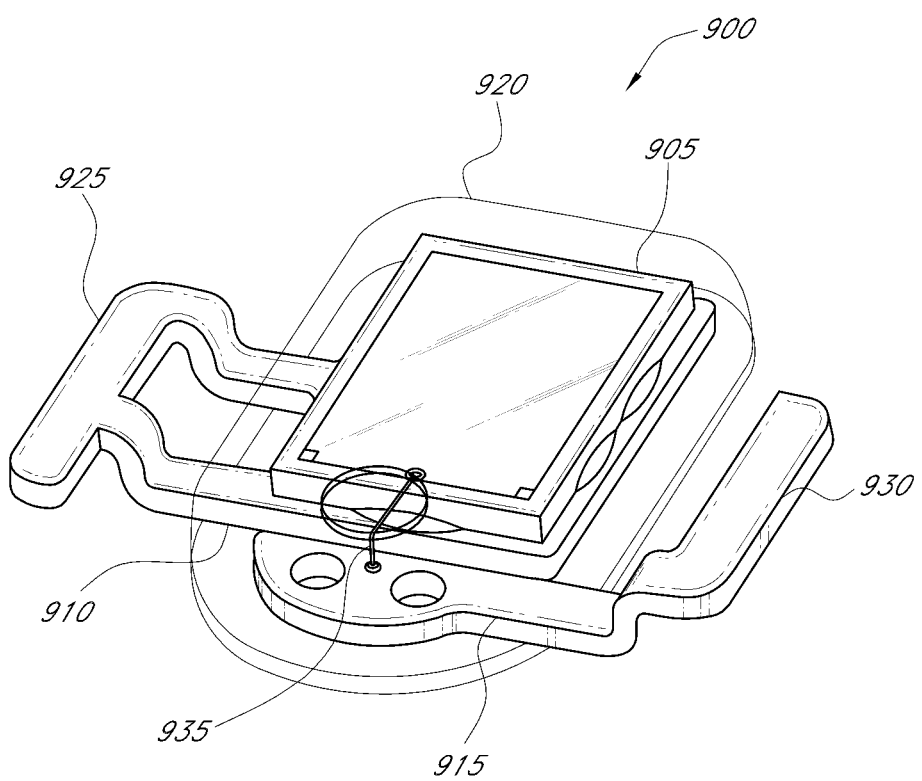
FIG. 9 illustrates a perspective view of a tissue facing side of an embodiment of a detector.

FIG. 9 illustrates a perspective view of a tissue facing side of an embodiment of a detector 900. The detector comprises a sensor 905 and a first lead frame 910 and a second lead frame 915. The detector can be electrically and/or mechanically coupled to the first lead frame 910. An encapsulate 920 can surround the sensor and portions of the lead frames.

In some embodiment, the lead frames 910, 915 are electrically isolated by the encapsulate 920. A wire bond 935 can connect the sensor 905 to the second lead frame 915. Lead frames can be incorporated in the encapsulate, for example, during manufacture.

In some embodiments, each lead frames can protrude outward to the sides or edges of the encapsulate 1020. The protruding portions 1025, 1030 allow electrical connections to be formed with wires, conductive substrates, or other conductive material for transmitting electrical signals to and/or from a monitor. Electrical coupling can be, for example, soldering, wire bonding, die bonding, or other suitable forms of electrical connection.

Figure 10:
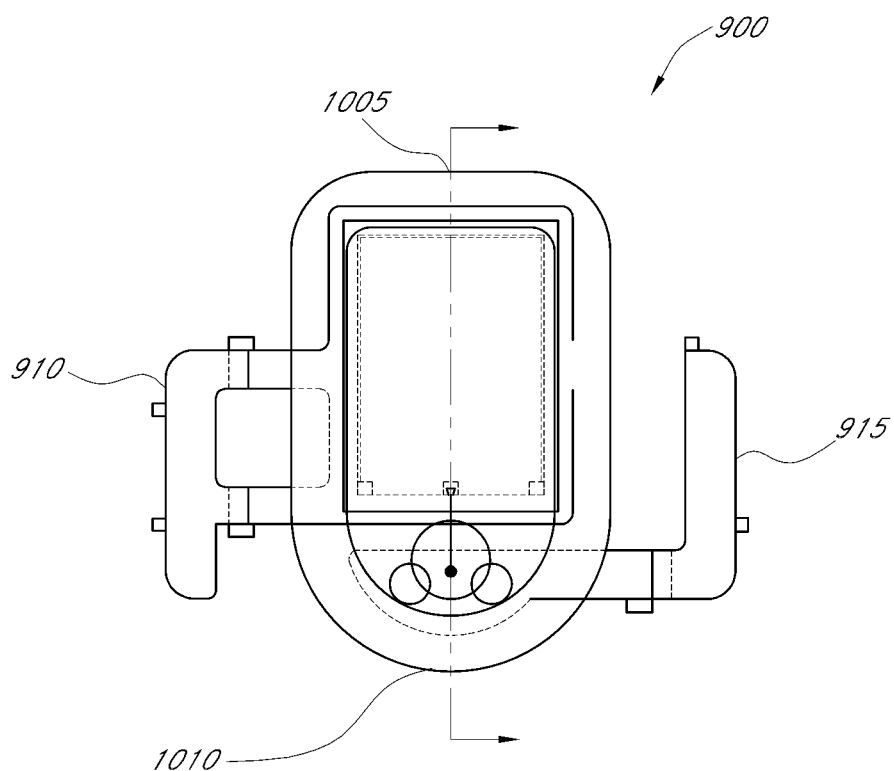
FIG. 10 illustrates a top view of the detector embodiment of FIG. 9.

FIG. 10 illustrates a top view of the detector 900 embodiment of FIG. 9. As described above for FIG. 5A, by forming the leads alongside the detector between a distal 1010 and a proximal 1005 of the detector, flex at the connection points to wires or other conductive material can be inhibited.

Figure 11:
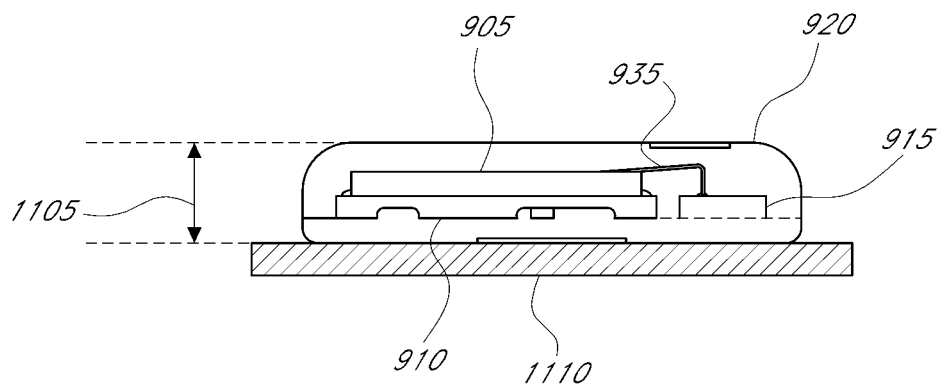
FIG. 11 illustrates a cross-sectional view of the detector embodiment of FIG. 9.

FIG. 11 illustrates a cross-sectional view of the detector embodiment of FIG. 9. The detector 905 on the first frame 910 can be connected to the second frame by a reverse wire bond 935. The reverse wire bond allows the formation of a lower-profile sensor as described above. In one embodiment, the height of the lead frame 915, wire bond 935, and thickness of the encapsulate 920 determine the profile height 1105 of the detector component. In some embodiments, the detector can be coupled to a sensor portion 1110, such as a sensor body, a tape layer, or the like, on the detector side opposite the tissue site. In some embodiments, another sensor portion, such as a cover, tape layer, or the like, can cover the tissue site side of the detector.

Of course, the foregoing embodiments are given by way of example and not limitation. Other variations of encapsulate formation, sensor emitter configuration, and/or detector configurations will be understood by those of skill in the art from the present disclosure. For example, the cavity can be different shapes, sizes, or have different relative positions to the encapsulate. Cavity sides can be straight on some sides and a different shapes such as diagonal on other sides. The relative height of a sensor component or cavity can change. In another example, the sensor emitter and/or detector can have three, four, or more leads and/or three, four or more lead frames. These combinations do not provide an extensive list of possible substitutions or modifications that will be apparent to the skilled artisan in view of the disclosure herein.

Figure 12:
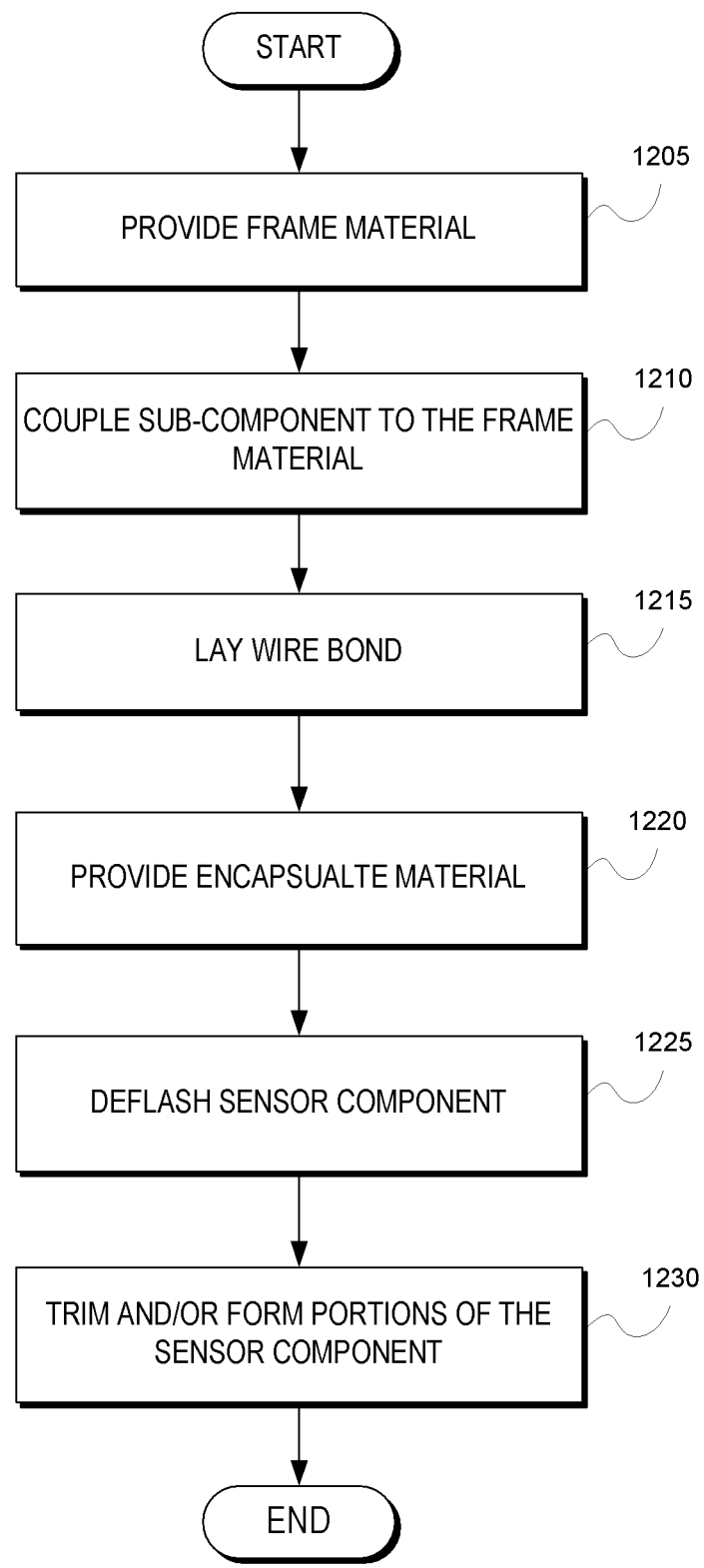
FIG. 12 illustrates a flow chart of an embodiment of a manufacturing process 1200 for assembling a sensor component.

FIG. 12 illustrates a flow chart of an embodiment of a manufacturing process 1200 for assembling a sensor component, such as an emitter or detector. The process 1200 can be used for manufacturing groups of components, such as the components used in the sensor embodiments described above. For example, the process 1200 may be used, in whole or in part, by one or more machines for manufacturing sensors. The one or more machines can be automated or controlled by an operator. In one embodiment, one or more blocks of the process 1200 can be performed manually by a person.

The process 1200 begins with block 1205, where frame material is provided. In some embodiments, the frame material can be partially shaped or formed. For example, a cavity can be formed in the frame material.

In block 1210, a sub-component, such as an LED, sensor component, or the like is coupled to the frame material. For example, the sub-component can be die bonded to the metallic frame using epoxy or solder. Coupling can be mechanical and/or electrical and can be accomplished by attachment methods such as, for example, painting, attaching, gluing, adhering, etching, fusing, mechanically fastening, or other attachment methods as would be understood by those of skill in the art from the present disclosure. Alternatively, the emitter can be grown or manufactured directly on the frame material. The epoxy or solder can be allowed to set before proceeding.

In block 1215, the wire bond is laid. The wire bond can connect the sub-component to the frame material. In some embodiments, the wire bond is a reverse wire bond as described above.

In block 1220, an encapsulate or mold compound, such as thermoset epoxy, polysiloxanes, thermoplastic, or the like is provided. The encapsulate can placed over the sub-component and lead frame and/or molded to form a desired shape. In some embodiments, the encapsulate is a transparent or translucent substance, allowing light to pass through. The encapsulate can wholly or partially cover the sub-component and frame material. As described above, the portions of the lead frame can protrude outside the encapsulate. The encapsulate can be allowed to set before proceeding with block 1225.

In block 1225, the sensor component can be deflashed in order to etch out the sensor component. For example, the lead frame can be etched out of the frame material.

In block 1230, the sensor component can be trimmed out of excess frame material. Optionally, portions of the sensor component can be further shaped or formed. For example, the connection points of the sensor leads can be formed from the lead frame.

Those skilled in the art will recognize from the disclosure that other sensor components such as those previously disclosed, or entire detector and/or emitter assemblies can be manufactured together to reduce cost or increase efficiency. Manufacturing components in groups reduces costs, for example, by reducing the number of assembly steps. In an embodiment, a group of lead frames is stamped from a single sheet of lead frame material and later separated into individual components. A group of sensor components, such as detectors or emitters, can be designed for batch assembly, for example, with cutouts that allow for ease in separation of individual sensor components such as by mechanically snapping the sensor components apart or by otherwise applying separating force. Those skilled in the art will recognize from the disclosure that in addition to cutouts, for example, the group of sensor components can be scored, cut, grooved, or otherwise prepared for separation to aid in manufacturing a group of sensor components.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Although the foregoing disclosure has been described in terms of certain preferred embodiments, other embodiments will be apparent to those of ordinary skill in the art from the disclosure herein. For example, although disclosed with respect to a pulse oximetry sensor, the ideas disclosed herein can be applied to other sensors such as ECG/EKG sensor, blood pressure sensors, or any other physiological sensors. Additionally, the disclosure is equally applicable to physiological monitor attachments other than a sensor, such as, for example, a cable connecting the sensor to the physiological monitor. Additionally, other combinations, omissions, substitutions and modifications will be apparent to the skilled artisan in view of the disclosure herein. It is contemplated that various aspects and features of the disclosure described can be practiced separately, combined together, or substituted for one another, and that a variety of combination and subcombinations of the features and aspects can be made and still fall within the scope of the disclosure. For example, the configurations described for the sensor emitter can be applied to the detector or other sensor components and vice versa. Furthermore, the systems described above need not include all of the modules and functions described in the preferred embodiments. Accordingly, the present disclosure is not intended to be limited by the recitation of the preferred embodiments, but is to be defined by reference to the appended claims.

What is claimed is:

1. A non-invasive physiological sensor configured to be used in a patient monitoring system, the physiological sensor configured to monitor a physiological parameter at a tissue site, the physiological sensor comprising:
    at least one light emitting element configured to transmit light at a plurality of wavelengths, wherein a portion of the light is transmitted towards the tissue site and a portion of the light is transmitted in a different direction from the tissue site;
    at least one reflective frame positioned at least partially on one side of the light emitting element and electrically connected to the light emitting element, the at least one reflective frame being electrically conductive and comprising a cavity, the cavity configured to redirect at least a portion of the light transmitted in a different direction from the tissue site to the tissue site; and
    an encapsulate surrounding at least a portion of the reflective frame and the at least one light emitting element, the encapsulate configured to allow at least some of the light transmitted by the at least one light emitting element to pass through, the encapsulate comprising a top, a bottom and at least one edge.

2. The non-invasive physiological sensor of claim 1, wherein the at least one reflective frame comprises a first frame and a second frame, the first frame separate from the second frame.

3. The non-invasive physiological sensor of claim 2, wherein the first and the second frame are electrically connected through one or more wires, the first frame and second frame configured into an inverse parallel circuit.

4. The non-invasive physiological sensor of claim 2, wherein the first and the second frame are configured into an inverse parallel circuit.

5. The non-invasive physiological sensor of claim 2, wherein the first frame comprises a first conductive lead and the second frame comprises a second conductive lead.

6. The non-invasive physiological sensor of claim 2, wherein the cavity is formed on portions of the first frame and second frame.

7. The non-invasive physiological sensor of claim 1, wherein the encapsulate comprises an at least semi-transparent material.

8. The non-invasive physiological sensor of claim 1, wherein the at least one light emitting element comprises a first light emitting element configured to transmit red wavelength light and a second light emitting element configured to transmit infrared wavelength light.

9. The non-invasive physiological sensor of claim 1, wherein the at least one reflective frame comprises a conductive lead protruding from the edge of the encapsulate, the conductive lead configured to accept an electrical connection with a conductive material.

10. The non-invasive physiological sensor of claim 1, wherein the at least one reflective frame provide operating current to the light emitting element.

11. A non-invasive physiological sensor configured to be used in a patient monitoring system, the physiological sensor comprising:
    an at least semi-rigid encapsulate surrounding at least a portion of a sensor component, the encapsulate having a top, a bottom, and at least one edge;
    an at least semi-flexible substrate layer, the encapsulate coupled to the substrate layer, wherein the encapsulate inhibits flexing of at least a portion of the substrate layer around the encapsulate; and
    a conductive lead, the conductive lead protruding from the at least one edge of the encapsulate, the conductive lead located along the flex-inhibited portion of the substrate layer, the conductive lead electrically connected to the sensor component within the encapsulate and including a reflective cavity configured to redirect at least a portion of light transmitted by the sensor component toward a tissue site,
    wherein the encapsulate is configured to inhibit flexing of a wire coupled to the conductive lead.

12. The non-invasive physiological sensor of claim 11, wherein the conductive lead extends along the at least one edge of the encapsulate, the conductive lead configured to inhibit flexing of the substrate layer.

13. The non-invasive physiological sensor of claim 11, wherein the encapsulate comprises a disk shape.

14. The non-invasive physiological sensor of claim 11, wherein the encapsulate comprises a cuboid shape.

15. The non-invasive physiological sensor of claim 11, wherein the substrate layer comprises one or more tape layers.

16. The non-invasive physiological sensor of claim 11, wherein the sensor component comprises at least one emitter.

17. The non-invasive physiological sensor of claim 11, wherein the sensor component comprises an emitter.

18. The non-invasive physiological sensor of claim 11, wherein the semi-flexible substrate comprises at least one wire for coupling with the conductive lead.

19. The non-invasive physiological sensor of claim 11, wherein the conductive lead provides operating current to the sensor component.

* * * * *